United States Patent
Ejiri et al.

(10) Patent No.: US 11,060,065 B2
(45) Date of Patent: Jul. 13, 2021

(54) TISSUE STRUCTURE AND PREPARATION METHOD THEREOF

(71) Applicants: Corning Incorporated, Corning, NY (US); Public University Corporation Yokohama City University, Yokohama (JP)

(72) Inventors: Yoko Ejiri, Tsukuba (JP); Satoru Ayano, Tsukuba (JP); Naoto Fukuhara, Tsukuba (JP); Hideki Taniguchi, Yokohama (JP); Takanori Takebe, Yokohama (JP)

(73) Assignees: Corning Incorporated, Corning, NY (US); PUBLIC UNIVERSITY CORPORATION YOKOHAMA CITY UNIVERSITY, Kanagawa (JP)

( * ) Notice: Subject to any disclaimer, the term of this patent is extended or adjusted under 35 U.S.C. 154(b) by 107 days.

(21) Appl. No.: 14/897,161

(22) PCT Filed: Jun. 9, 2014

(86) PCT No.: PCT/JP2014/003067
§ 371 (c)(1),
(2) Date: Dec. 9, 2015

(87) PCT Pub. No.: WO2014/199622
PCT Pub. Date: Dec. 18, 2014

(65) Prior Publication Data
US 2016/0122722 A1    May 5, 2016

(30) Foreign Application Priority Data

Jun. 10, 2013   (JP) .............................. JP2013-122190

(51) Int. Cl.
| | |
|---|---|
| *C12N 5/071* | (2010.01) |
| *C12M 1/00* | (2006.01) |
| *C12M 1/42* | (2006.01) |
| *C12Q 1/6837* | (2018.01) |

(52) U.S. Cl.
CPC ........... *C12N 5/0697* (2013.01); *C12M 23/20* (2013.01); *C12M 35/08* (2013.01); *C12N 5/069* (2013.01); *C12Q 1/6837* (2013.01); *C12N 2502/13* (2013.01); *C12N 2502/1388* (2013.01); *C12N 2502/28* (2013.01)

(58) Field of Classification Search
None
See application file for complete search history.

(56) References Cited

U.S. PATENT DOCUMENTS

| | | | |
|---|---|---|---|
| 6,027,695 | A | 2/2000 | Oldenburg et al. |
| 6,284,451 | B1 | 9/2001 | Funatsu et al. |
| 2012/0058491 | A1 | 3/2012 | Kume et al. |
| 2012/0115226 | A1 | 5/2012 | Stachelsheid et al. |
| 2013/0296183 | A1 | 11/2013 | Eggan et al. |
| 2014/0227784 | A1 | 8/2014 | Ejiri et al. |
| 2014/0289877 | A1 | 9/2014 | Taniguchi et al. |

FOREIGN PATENT DOCUMENTS

| | | |
|---|---|---|
| CN | 1490400 A | 4/2004 |
| EP | 2 169 051 A1 | 3/2010 |
| EP | 2 759 592 A1 | 7/2014 |
| EP | 2 762 558 A1 | 8/2014 |
| JP | 9-56814 A | 3/1997 |
| JP | 2000287680 A | 10/2000 |
| JP | 2004-166717 A | 6/2004 |
| JP | 2012-529901 A | 11/2012 |
| JP | WO 2013/042360 A1 | 3/2013 |
| JP | WO 2013/047639 A1 | 4/2013 |
| WO | WO 2007/058105 A1 | 5/2007 |
| WO | WO 2008/066199 A1 | 6/2008 |
| WO | WO 2008/149807 A1 | 12/2008 |
| WO | WO 2010/149597 A2 | 12/2010 |
| WO | WO 2010/149597 A3 | 12/2010 |
| WO | WO 2012/037456 A1 | 3/2012 |
| WO | 2013047974 A1 | 4/2013 |

OTHER PUBLICATIONS

Welty et al (BMC Molecular Biology, Feb. 2013, vol. 14, No. 6, pp. 1-11).*
Extended European Search Report dated Nov. 18, 2016 in patent application No. 14811401.0.
Momotaro Ishikawa et al., "Reconstitution of hepatic tissue architectures from fetal liver cells obtained from a three-dimensional culture with a rotating wall vessel bioreactor" Journal of Bioscience and Bioengineering, vol. 111, No. 6, XP028224328, Jan. 31, 2011, pp. 711-218.
Takanori Takebe et al., "Vascularized and functional human liver from an iPSC-derived organ bud transplant" Nature, vol. 449, XP007922049, Jul. 3, 2013, 5 pages.
Search Report and Written Opinion dated Jan. 19, 2017 in Singaporean Patent Application No. 11201508747X.
Maya Schuldiner, et al., "Effects of eight growth factors on the differentiation of cells derived from human embryonic stem cells" PNAS, vol. 97, No. 21, Oct. 10, 2000, pp. 11307-11312.
Basak E Uygun, et al., "Organ reengineering through development of a transplantable recellularized liver graft using decellularized liver matrix" Nature Medicine, vol. 16, No. 7, Jul. 2010, pp. 814-821.

(Continued)

*Primary Examiner* — Nancy J Leith
(74) *Attorney, Agent, or Firm* — Cynthia A Neal; Annie J. Kock

(57) ABSTRACT

A tissue structure for enabling comprehensive understanding of gene patterns of mature cells and a method of preparing the tissue structure are provided. A tissue structure is obtained by co-culturing an endodermal, ectodermal, or mesodermal cell derived from a stem cell and at least one cell and/or factor selected from the group consisting of a vascular cell, a mesenchymal cell, a factor secreted by a vascular cell, a factor secreted by a mesenchymal cell, and a factor secreted when both a vascular cell and a mesenchymal cell exist. A value obtained by assay of a plurality of functions using a Pearson product-moment correlation coefficient is closer to a value of a cell or biological tissue sampled from an adult than a value of a cell or biological tissue sampled from a fetus.

16 Claims, 7 Drawing Sheets

(56) References Cited

OTHER PUBLICATIONS

Marta Szabat, et al., "Kinetics and genomic profiling of adult human and mouse β-cell maturation" Islets, vol. 3, No. 4, 2011, pp. 175-187.

Guoqiang Gu, et al., "Global expression analysis of gene regulatory pathways during endocrine pancreatic development" Development 131 Research article, 2004, pp. 165-179.

Francesco Pampaloni, et al., "The third dimension bridges the gap between cell culture and live tissue" Nature Reviews Molecular Cell Biology, vol. 8, Oct. 2007, pp. 839-845.

Markus Rimann, et al., "Synthetic 3D multicellular systems for drug development" Current Opinion in Biotechnology, vol. 23, 2012, pp. 803-809.

International Search Report dated Sep. 2, 2014 in PCT/JP2014/003067.

Combined Office Action and Search Report dated Jun. 7, 2017 in Chinese Patent Application No. 201480033286.1 (with English translation relevant part and English translation of categories of cited documents).

Combined Office Action and Search Report dated Apr. 11, 2018 in Chinese Patent Application No. 201480033286.1 with partial English translation and English translation of categories of cited documents, 21 pages.

Horman, "3D high-content analysis of spheroids", Genetic Engineering & Biotechnology News 33(16) 2013. Retrieved from: https://www.genengnews.com/magazine/3d-high-content-analysis-of-spheroids.

Joo et al. "Angiopoietin-1 promotes endothelial differentiation from embryonic stem cells and induced pluripotent stem cells," Blood 25; 118(8) 2011, pp. 2094-2104.

Matsumoto et al. "Liver Organogenesis Promoted by Endothelial Cells Prior to Vascular Function", Science 19, 294(5542) 2001, pp. 559-563.

Peters et al. "Efficient Generation of Multipotent Mesenchymal Stem Cells from Umbilical Cord Blood in Stroma-Free Liquid Culture", PLoS One 30; 5(12) 2010, e15689.

Takebe et al. "Massive and Reproducible Production of Liver Buds Entirely from Human Pluripotent Stem Cells", Cell Reports, 21, 2017, pp. 2661-2670.

Takebe, "Creation of functional human organs using pluripotent stem cells", Japan Medical Society, 2012, 188, pp. 10-12 (translation attached).

Takebe et al. "Self-organization of human hepatic organoid by recapitulating organogenesis in vitro," Transplantation Proceedings 44(4) 2012, pp. 1018-1020.

Takebe et al. "Vascularized and complex organ buds from diverse tissues via mesenchymal cell-driven condensation", Cell Stem Cell 16(5) 2015, pp. 556-565.

European Patent Application No. 19212109.3; Extended Search Report dated Jan. 10, 2020; European Patent Office; 14 Pgs.

Wang et al., "Comparison of differentiated endothelial cells from the embryonic stem cells with human umbilical vein endothelial cells", Journal of Central South University. Medical sciences, vol. 42, 2017, pp. 374-379 (English Abstract Submitted).

Office Action dated Nov. 21, 2017 in Japanese Patent Application No. 2015-522539 (with unedited computer generated English translation of relevant part).

Canadian Patent Application No. 2,913,559, Office Action dated Feb. 18, 2021, 4 pages; Canadian Patent Office.

Huang et al., " Microfluidic Cell Culture System Studies and Computational Fluid Dynamics", Mathematical and Computer Modelling 2010, vol. 52, pp. 2036-2042.

* cited by examiner

TISSUE STRUCTURE AND PREPARATION METHOD THEREOF

TECHNICAL FIELD

The present invention relates to a tissue structure having a function equivalent to that of a mature tissue from a stem cell, for example an undifferentiated cell, such as an induced pluripotent stem cell and an embryonic stem cell, and a method of preparing the tissue structure.

BACKGROUND ART

In recent years, attempts have been made to differentiate pluripotent stem cells, such as iPS cells, which have an ability to differentiate into various functional cells, into cells having functions specific to an organ or cell of interest, and to use the cells for drug discovery screening and regenerative medicine (for example, Non Patent Literature 1). However, only some of the in vivo functions can be reproduced in the cells, and the reproduced functions in the cells are extremely lower than the functions in vivo.

In a drug discovery screening test, it is required to show drug susceptibility and toxic reaction that are similar to those obtained in a test performed in a living body, that is, a so-called in vivo test. The above-mentioned prior art is insufficient for use in such a case. Therefore, there is a demand for more mature cells, i.e., cells having functions whose expression level is equivalent to that of functions in vivo.

In the field of regenerative medicine, organ transplantation and artificial organ transplantation are carried out. However, there are problems with transplantations such as shortage of donors and transplant rejection. For example, in clinical practice, organ transplantation and replacement with artificial organs are carried out to treat severe organ failures. However, there are problems with organ transplantations such as rejections and critical shortage of donors, and artificial organs are only capable of replacing some of the required function for a short period of time (for example, Patent Literature 1 and 2). Thus, some fundamental problems have not been solved. With respect to creation of human tissues, though a method in which terminally differentiated cells are seeded on a support (scaffolding) has been conceived, no technique has ever been established for creating an organ with complex higher functions such as a liver (Non Patent Literature 2).

While there is a demand for terminally differentiated mature a cell or biological tissue, no technique has ever been established for creating them. An example in which a differentiated cell of an adult and a differentiated cell of related art are compared with each other with respect to liver functions will be described below.

As is apparent from the fact that cytochrome P450, which is one of the drug-metabolizing enzymes in hepatocytes, has 57 types of genes, cells have an extremely large number of functions. These functions work at the same time or as needed in order to sustain life.

It has been confirmed that expression levels of 80 genes in hepatocytes increase in the process of growing to an adult from a fetus period. Non Patent Literature 3 and 4 disclose that the gene expression profile changes as cells mature in pancreas in the process of development.

CITATION LIST

Patent Literature

[Patent Literature 1] Japanese Unexamined Patent Application Publication No. H09-56814

[Patent Literature 2] Japanese Unexamined Patent Application Publication No. 2004-166717

[Patent Literature 3] International Patent Publication No. WO 2013/047639

[Patent Literature 4] International Patent Publication No. WO 2007/058105

[Patent Literature 5] International Patent Publication No. WO 2008/066199

Non Patent Literature

[Non Patent Literature 1] Maya Schuldiner, et al., "Effects of eight growth factors on the differentiation of cells derived from human embryonic stem cells", PNAS, 97 vol. 21, Oct. 10, 2000 (Published online), pp. 11307-11312

[Non Patent Literature 2] Basak E Uygun, et al., "Organ reengineering through development of a transplantable recellularized liver graft using decellularized liver matrix", Nat Med, 16(7), Jun. 13, 2010 (Published online), pp. 814-820

[Non Patent Literature 3] Marta Szabat, et al., "Kinetics and genomic profiling of adult human and mouse β-cell maturation", Islets 3:4, July/August 2011, pp. 175-187

[Non Patent Literature 4] Guoqiang Gu, et al., "Global expression analysis of gene regulatory pathways during endocrine pancreatic development" Research article, Sep. 30, 2003, pp. 165-178

[Non Patent Literature 5] Francesco Pampaloni, et al., "The third dimension bridges the gap between cell culture and live tissue", Nature reviews molecular cell biology volume 8, October 2007, pp. 839-845

[Non Patent Literature 6] Markus Rimann, et al., "Synthetic 3D multicellular systems for drug development" Current Opinion in Biotechnology 2012 23, 2012, pp. 1-7

SUMMARY OF INVENTION

Technical Problem

For example, organ buds are disclosed in Patent Literature 3; a method for inducing islet cells from undifferentiated cells is disclosed in Patent Literature 4; and a method for inducing insulin-secreting cells from undifferentiated cells is disclosed in Patent Literature 5. However, in any of these techniques, the presence or absence of differentiation is judged on a limited number of evaluation indices by focusing only on a part of the cell functions. Accordingly, it cannot be determined that the cells or organs thus obtained have reached a so-called mature level at which a number of gene patterns are expressed as mentioned above.

Therefore, in the case of determining the effect, the toxicity, and the like of a drug by using the cells or organs that are determined based on the evaluation indices of related art, there is a problem that a reaction within a living body cannot be accurately predicted, and there is also a problem that an artificial organ cannot work satisfactorily in a living body.

The present inventors have found that it is important to comprehensively understand the gene patterns and the expression of protein in terminally differentiated mature a cell or biological tissue, in order to avoid the above-mentioned problems.

Solution to Problem

The present inventors have invented a novel tissue structure obtained using the similarity of gene expression patterns and expressions of protein in terminally differentiated mature a cell or biological tissue as indices, and a method of preparing the tissue structure.

A tissue structure according to a one aspect of the present invention is a tissue structure obtained by co-culturing an endodermal, ectodermal, or mesodermal cell derived from a stem cell and at least one cell and/or factor selected from the group consisting of a vascular cell, a mesenchymal cell, a factor secreted by a vascular cell, a factor secreted by a mesenchymal cell, and a factor secreted when both a vascular cell and a mesenchymal cell exist. A value obtained by assay of a plurality of functions using a Pearson product-moment correlation coefficient is closer to a value of a cell or biological tissue sampled from an adult than a value of a cell or biological tissue sampled from a fetus.

In the tissue structure according to the one aspect of the present invention, it is preferable that the plurality of functions are expression levels of ten or more types of genes and the ten or more types of genes are genes whose gene expression levels in the tissue structure vary by two-fold or more relative to those gene expression levels in the endodermal, ectodermal, or mesodermal cell derived from the stem cell. For example, preferably, a gene expression level is a value obtained by an analysis using a DNA chip on which all gene segments are immobilized, and that the ten or more types of genes are all genes whose gene expression levels in the tissue structure vary by two-fold or more relative to those gene expression levels in the endodermal, ectodermal, or mesodermal cell derived from the stem cell.

Further, in the tissue structure according to the one aspect of the present invention, it is preferable that the plurality of functions are amounts of proteins measured for ten or more types of proteins, and that the ten or more types of proteins are all proteins whose amounts in the tissue structure vary by 20% or more relative to amounts of those proteins in the endodermal, ectodermal, or mesodermal cell derived from the stem cell. Preferably, the tissue structure has a spheroid shape and the spheroid has a diameter in a range from 50 μm to 2 mm.

It is also preferable that the plurality of functions are functions specific to a liver or pancreas.

A one aspect of the present invention is a method of preparing a tissue structure, including: (1) preparing a cultured form by co-culturing an endodermal, ectodermal, or mesodermal cell derived from a stem cell and at least one cell and/or factor selected from the group consisting of a vascular cell, a mesenchymal cell, a factor secreted by a vascular cell, a factor secreted by a mesenchymal cell, and a factor secreted when both a vascular cell and a mesenchymal cell exist; (2) performing an assay of a plurality of functions of the cultured form by using a Pearson product-moment correlation coefficient; and (3) picking, as a tissue structure, a cultured form in which a value obtained by the assay is closer to a value of a cell or biological tissue sampled from an adult than a value of a cell or biological tissue sampled from a fetus.

In the method of preparing a tissue structure according to the one aspect of the present invention, it is preferable that the plurality of functions are expression levels of ten or more types of genes; the ten or more types of genes be genes whose gene expression levels in the tissue structure vary by two-fold or more relative to a gene expression level of the endodermal, ectodermal, or mesodermal cell derived from the stem cell; and the picking of the tissue structure include: measuring gene expression levels of the cultured form and the endodermal, ectodermal, or mesodermal cell derived from the stem cell; and selecting a cultured form including ten or more types of genes whose gene expression levels in the cultured form vary by two-fold or more relative to those gene expression levels in the endodermal, ectodermal, or mesodermal cell derived from the stem cell. For example, preferably, when gene expression levels in the tissue structure and the endodermal, ectodermal, or mesodermal cell derived from the stem cell are analyzed using a DNA chip on which all gene segments are immobilized, the ten or more types of genes are all genes whose gene expression levels in the tissue structure vary by two-fold or more relative to those gene expression levels in the endodermal, ectodermal, or mesodermal cell derived from the stem cell.

Further, in the method of preparing a tissue structure according to the one aspect of the present invention, it is preferable that the plurality of functions are amounts of proteins measured for ten or more types of proteins; the ten or more types of proteins are all proteins whose amounts in the tissue structure vary by 20% or more relative to amounts of those proteins in the endodermal, ectodermal, or mesodermal cell derived from the stem cell; and the picking of the tissue structure include: measuring amounts of proteins in the cultured form and the endodermal, ectodermal, or mesodermal cell derived from the stem cell; and selecting a cultured form including ten or more types of proteins whose amounts in the cultured form vary by two-fold or more relative to amounts of those proteins in the endodermal, ectodermal, or mesodermal cell derived from the stem cell.

In the method of preparing a tissue structure according to the one aspect of the present invention, the co-culture step preferably includes the steps of: forming an aggregate; forming an organ bud; and further culturing the organ bud for maturation. In addition, in the steps of forming an aggregate, forming an organ bud, and further culturing the organ bud for maturation, cells are preferably combined to form an aggregate. More preferably, in the steps of forming an aggregate, forming an organ bud, and further culturing the organ bud for maturation, cells are combined to form a cluster having a spheroid shape.

In the method of preparing a tissue structure according to the one aspect of the present invention, it is preferable that a spheroid formed by the cells have a diameter in a range from 50 μm to 2 mm. The endodermal, ectodermal, or mesodermal cell derived from the stem cell is preferably a cell selected from the group consisting of a cell derived from fetal stem cell and a cell derived from an induced pluripotent stem cell. More preferably, the endodermal, ectodermal, or mesodermal cell derived from the stem cell is a cell capable of differentiating into an endoderm lineage cell from a cell derived from an induced pluripotent stem cell.

It is also preferable that the plurality of functions are functions specific to a liver or pancreas.

In the method of preparing a tissue structure according to the one aspect of the present invention, the tissue structure is preferably cultured using a microchamber having an equivalent diameter in a range from 20 μm to 2.5 mm and a depth in a range from 20 μm to 1000 μm. In addition, the tissue structure is preferably cultured using a culture chamber having a culture surface which is a cell non-adhesive surface. Furthermore, the culture surface of the culture chamber is preferably coated with a polymer selected from the group consisting of a phospholipid, a phospholipid-polymer complex, poly(2-hydroxyethyl methacrylate) (PHEMA), polyvinyl alcohol, agarose, chitosan, polyethyleneglycol, and albumin, or a combination thereof, the culture surface being a surface in contact with cells.

In the method of preparing a tissue structure according to the one aspect of the present invention, it is preferable that a vascular cell: an endodermal, ectodermal, or mesodermal cellderived from a stem cell: and a mesenchymal cell are co-cultured at a ratio of 10:7-10:1-2, and that the cells are seeded at a density of 20 to 2000 cells per microchamber. The microchamber is preferably formed of a bottom portion and an opening. The opening is preferably defined by a wall that surrounds an area from a boundary between the opening and the bottom portion to an end of the opening, the wall having a taper angle in a range from 1 to 20 degrees. The bottom portion preferably has either a hemispherical shape or a truncated cone shape.

Advantageous Effects of Invention

According to one embodiment, it is possible to provide a tissue structure enabling for comprehensive understanding of the expression of proteins and gene patterns of a terminally differentiated mature cell (a tissue structure differentiated and induced from an undifferentiated cell) or a biological tissue, and a method of preparing the tissue structure.

DESCRIPTION OF EMBODIMENTS

Figure 1:
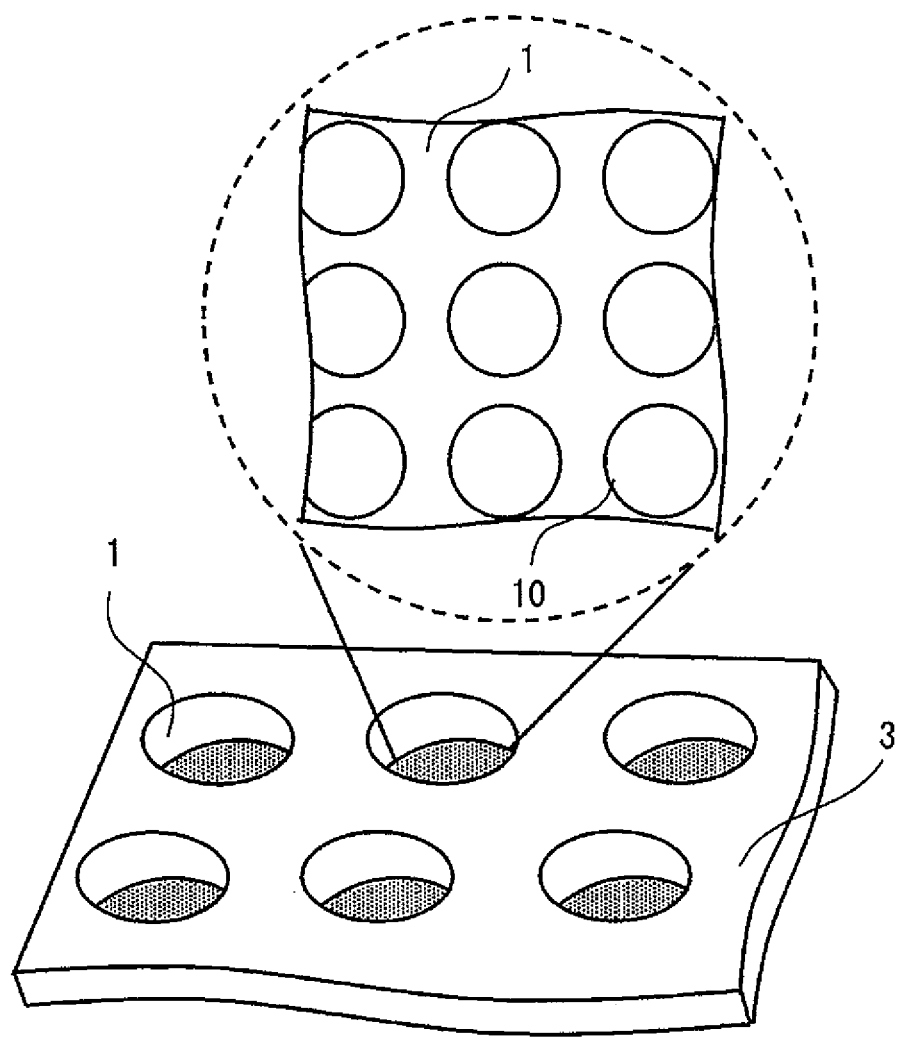
FIG. 1 is a diagram showing an example of a culture chamber according to an embodiment.

Embodiments will be described below with reference to the drawings. To clarify the explanation, omissions and simplifications are made as necessary in the following description and the drawings. Throughout the drawings, the constituent elements having the same configuration or function, or corresponding parts are denoted by the same reference numerals, and the descriptions thereof are omitted.

A tissue structure according to one of the embodiments is a mature cell or a biological tissue which is differentiated in a test tube. The tissue structure is prepared using, as an index, the similarity of gene expression patterns of mature a cell or biological tissue which are derived (sampled) from an adult. Functions of mature cells or functions produced by mature cells are derived from gene expression patterns. For this reason, "gene expression patterns" can be referred to as "a plurality of functions".

During physiological organogenesis processes, organogenesis accompanied by autonomous constitution of tissue structures and cell differentiation progresses through close interactions of organ cells with vascular cells and undifferentiated mesenchymal cells.

In one of the embodiments, the histogenetic capacity is induced in the cell which achieved initial differentiation by artificially reproducing those early processes of organogenesis to thereby induce the initial differentiation via interactions among a plurality of cell lineages and induce the histogenetic capacity of the cell. Further, the one of the embodiments intends to prepare a tissue which is composed of a cell and a vascular system in the culture chamber by culturing and maturing a cell or a biological tissue in a culture chamber via a differentiated cell or a biological tissue, such as an organ bud, which grows into, for example, a tissue or an organ, in which the plurality of functions of the mature cell are expressed.

Explanation of Tissue Structure

A tissue structure according to one of the embodiments is a tissue structure obtained by co-culturing an endodermal, ectodermal, or mesodermal cell derived from a stem cell and at least one cell and/or factor selected from the group consisting of a vascular cell, a mesenchymal cell, a factor secreted by a vascular cell, a factor secreted by a mesenchymal cell, and a factor secreted when both a vascular cell and a mesenchymal cell exist. Additionally, the tissue structure shows a value obtained by assay for the values of a plurality of functions using a Pearson product-moment correlation coefficient which is closer to the value of a cell sampled from an adult or a biological tissue sampled from an adult than the value of a cell sampled from a fetus or a biological tissue sampled from a fetus.

The tissue structure having the above-mentioned features with respect to the plurality of functions is formed by forming an organ bud and maturing the organ bud as a result of co-culturing at least two types (preferably, three types) of cells. As described in detail later, an organ bud is a structure which can differentiate into an organ as a result of maturing.

The following terms are used in this specification.

The term "biological tissue" refers to a unit of a structure including several specific types of cells which aggregate in a predetermined pattern. The biological tissue has a unified role as a whole. For example, each organ in a living body is formed by several types of tissues which aggregate in a predetermined pattern. A cell cluster (cell group) which is formed of differentiated cells and has an arbitrary function is herein referred to as a tissue.

The term "an endodermal, ectodermal, or mesodermal cell derived from a stem cell" (hereinafter referred to as "a triploblastic cell derived from a stem cell") will be described below.

The term "stem cell" refers to a cell which includes a cell selected from the group consisting of a viviparous stem cell (ES cell) and an induced pluripotent stem cell (iPS cell), has infinite proliferative potential, and is capable of differentiating into any of endodermal, mesodermal, and ectodermal organs.

The term "endodermal cell" refers to a cell capable of differentiating into a mesodermal organ, such as a liver, pancreas, intestinal tract, lung, thyroid, parathyroid, or urinary tract.

The term "ectodermal cell" refers to a cell capable of differentiating into an ectodermal organ such as a brain, spinal cord, adrenal medulla, epidermis, hair/nail/dermal-gland, sensory organ, peripheral nerve, or lens.

The term "mesodermal cell" refers to a cell capable of differentiating into a mesodermal organ such as a kidney, ureter, heart, blood, gonad, adrenal cortex, muscle, skeleton, dermis, connective tissue, or mesothelium.

That is, the term "a triploblastic cell derived from a stem cell" refers to a cell having the characteristics of an endodermal, ectodermal, or mesodermal organ derived from a cell selected from the group consisting of an ES cell and an iPS cell.

Whether a cell is one which can differentiate into an ectodermal organ, a mesodermal organ, or an endodermal organ can be confirmed by examining the expression of marker proteins (if any one or a plurality of the marker proteins are expressed, the cell can be judged to be a cell that can differentiate into an endodermal organ). For example, HHEX, SOX2, HNF4A, AFP, ALB, and the like are markers for a cell which can differentiate into a liver; PDX1, SOX17, SOX9, and the like are markers for a cell which can differentiate into a pancreas; CDX2, SOX9, and the like are markers for a cell which can differentiate into an intestinal tract; SIX2 and SALL1 are markers for a cell which can differentiate into a kidney; NKX2-5 MYH6, ACTN2, MYL7, and HPPA are markers for a cell which can differentiate into a heart; C-KIT, SCA1, TER119, and HOXB4 are markers for a cell which can differentiate into blood; and HNK1, AP2, NESTIN, and the like are markers for a cell which can differentiate into a brain or spinal cord.

The term "mesenchymal cell" refers to a connective tissue cell which exists mainly in a connective tissue derived from mesoderm and forms a support structure for a cell that functions in a tissue. The mesenchymal cell includes a cell that is destined to differentiate into a mesenchymal cell but has not differentiated into a mesenchymal cell. The mesenchymal cell used in the present invention may be a differentiated one or undifferentiated one. Whether a cell is a undifferentiated mesenchymal cell or not can be confirmed by examining the expression of marker proteins, such as Stro-1, CD29, CD44, CD73, CD90, CD105, CD133, CD271, or Nestin (if any one or a plurality of the marker proteins are expressed, the cell can be judged to be an undifferentiated mesenchymal cell). The mesenchymal cell in which all the markers described above are not expressed can be judged to be a differentiated mesenchymal cell. Among the terms used by those skilled in the art, the following are included in the mesenchymal cell in the present invention: a mesenchymal stem cell, mesenchymal progenitor cell, mesenchymal cell (R. Peters, et al. PLoS One. 30; 5 (12): e15689. (2010)), and so on. The mesenchymal cell derived from a human are mainly used, but an undifferentiated mesenchymal cell derived from a non-human animal, such as a mouse, a rat, a dog, a pig, and a monkey, may also be used.

The term "vascular cell" refers to a cell that constitutes a vascular endothelium, or a cell which can differentiate into such a cell. Whether a cell is a vascular cell or not can be confirmed by examining the expression of a marker protein such as TIE2, VEGFR-1, VEGFR-2, VEGFR-3, or CD41 (if any one or a plurality of the marker proteins are expressed, the cell can be judged to be a vascular cell). The vascular cell used in the present invention may be differentiated or undifferentiated. It can be confirmed whether the vascular cell is a differentiated cell or not by the expression of CD31 and CD144. Among the terms used by those skilled in the art, the following are included in the vascular cell of the present invention: an endothelial cell, umbilical vein endothelial cell, endothelial progenitor cell, endothelial precursor cell, vasculogenic progenitor, hemangioblast (H J. joo, et al. Blood. 25; 118 (8): 2094-104. (2011)), and so on. The vascular cell derived from a human are mainly used, but a vascular cell derived from a non-human animal such as a mouse, a rat, a dog, a pig, and a monkey may also be used.

The term "organ bud" refers to a structure which can differentiate into an organ as a result of maturing and includes three types of cells that are, a triploblastic cell derived from a stem cell, a vascular cell, and an undifferentiated mesenchymal cell, or a cell differentiated from those cells. Whether a structure is an organ bud or not can be confirmed by, for example, transferring the structure into a living body and examining whether the structure can differentiate into an organ of interest (if the structure differentiates into the organ of the interest, the structure can be judged to be an organ bud), and/or examining whether all the three types of cells described above are included in the structure (if all the three types of cells are included, the structure can be judged to be an organ bud). The organ bud may be one which differentiates into an organ such as a kidney, heart, lung, spleen, esophagus, stomach, thyroid, parathyroid, thymus, gonad, brain, or spinal cord. Preferably, the organ bud is one which differentiates into an endodermal organ such as one which differentiates into a liver (a liver bud), one which differentiates into a pancreas (a pancreatic bud), or one which differentiates into an intestinal tract. Whether a structure is an organ bud which differentiates into an endodermal organ or not can be confirmed by examining the expression of marker proteins (if any one or a plurality of the marker proteins described later are expressed, the structure can be judged to be an organ bud). For example, HHEX, SOX2, HNF4A, AFP, ALB, and the like are markers for a liver bud; PDX1, SOX17, SOX9, and the like are markers for a pancreatic bud; and CDX2, SOX9, and the like are markers for an organ bud which differentiate into an intestinal tract. Among the terms used by those skilled in the art, the following are included in the organ bud of the present invention: a liver bud, liver diverticula, liver organoid, pancreatic (dorsal or ventral) bud, pancreatic diverticula, pancreatic organoid, intestinal bud, intestinal diverticula, intestinal organoid (K. Matsumoto, et al. Science. 19; 294 (5542): 559-63 (2001)), and so on.

The term "a cell sampled from a fetus" refers to a cell sampled from a fetus which develops from an egg, communicates with its mother's body in some way, grows based on nutrients from the parent body, and is to be born after it is fully grown. For example, a cell sampled from a fetus includes a biological tissue of a fetal liver and commercially-available fetal liver cell.

The term "a cell sampled from an adult" refers to a cell sampled from a living body which has fully grown and is reproductive. A Cell sampled from an adult includes, for example, commercially-available human primary hepatocytes and biopsied biological tissues.

As "a cell or a biological tissue sampled from an adult", a cell derived from a human or an animal are available from manufacturers. Hepatocytes are available from Charles River Laboratories International, Inc. and KAC Co., Ltd.

A hepatocyte can also be sampled from an animal. For example, in the case of sampling a hepatocyte from a rat or a mouse, there is a method for separating a hepatocyte by a two-step collagenase perfusion method. In the case of using a rat, for example, a method can be used in which a cannula is inserted into the portal vein of the rat to remove blood using a phosphate buffer (pre-perfusate) heated to 37 degrees, and only a cell is collected by degradation of collagen with a Collagenase solution heated to 37 degrees.

"A cell or biological tissue sampled from a fetus" is commercially available. The cell or biological tissue is available from a cell bank or the like. For example, a cell or biological tissue are available from VERITAS Corporation.

The term "correlation coefficient" refers to a statistical index indicating a correlation (a degree of similarity) between two random variables. In principle, the correlation coefficient is dimentionless. When a value is a real number between −1 to 1 and the value is close to 1, the two random variables have a positive correlation, and when the value is close to −1, the two random variables have a negative correlation. When the value is close to 0 (zero), the correlation between the original random variables is weak. When the value is 1 or −1, the two random variables have a linearly dependent relationship. The term "correlation coefficient" generally refers to a Pearson product-moment correlation coefficient. The assay of the correlation coefficient is a parametric method which assumes a normal distribution of deviation. In addition, non-parametric methods, such as Spearman's rank correlation coefficient and Kendall rank correlation coefficient, which do not assume a normal distribution of deviations, are generally used.

"Pearson product-moment correlation coefficient" is used to check the linear relationship between two variables X and Y. The Pearson product-moment correlation coefficient is represented by a lower-case letter "r" and takes a range of $-1 \leq r \leq 1$. The case of "+(plus)" indicates a positive correlation, i.e., a positive relationship in which one variable increases while the other one also increases. The case of "−(minus)" indicates a negative relationship in which one variable increases while the other one decreases.

Explanation of a Plurality of Functions

The term "a plurality of functions" refers to functions included in a tissue structure, or functions which can be detected in a tissue structure. In one embodiment, for example, functions which can be measured by the gene expression level and the amount of protein are used. In particular, functions which vary when a triploblastic cell derived from a stem cell is differentiated into a tissue structure are used. Specifically, among the functions of the tissue structure, when the functions of a cell sampled from a fetus are compared with the functions of a cell sampled from an adult, the functions whose level varies more than the level of the other functions are used. A structure with a level of functions that is closer to that of a cell sampled from an adult than that of a cell sampled from a fetus is selected (picked) as the tissue structure.

In this case, a cell sampled from a fetus includes a cell sampled from a fetus and the biological tissue thereof, and a cell sampled from an adult includes a cells sampled from an adult and the biological tissue thereof.

For example, expression levels of ten or more types of genes can be used as the plurality of functions.

In the case of selecting the species of the genes, the species of the genes whose gene expression levels in the tissue structure vary by two-fold or more relative to those gene expression levels of an organ bud are included among those selected. In the case of selecting the species of the proteins, the species of the proteins whose amount of protein in the tissue structure varies by 20% or more relative to the amount of protein in an organ bud are included among those selected.

Alternatively, the ten or more types of genes include genes whose gene expression levels in the tissue structure vary by two-fold or more relative to those gene expression levels of a triploblastic cell derived from a stem cell. More specifically, a value obtained by an analysis using a DNA chip on which all gene segments are immobilized is used as a gene expression level. The ten or more types of genes include all genes whose gene expression levels in the tissue structure vary by two-fold or more relative to those gene expression levels of a triploblastic cell derived from a stem cell.

The reason why the expression levels of ten or more types of genes are used is that numbers are set to determine the maturation of a tissue structure from a triploblastic cell derived from a stem cell, based on the expression levels of the genes.

As another example, the amounts of proteins measured for ten or more types of proteins can be used as the plurality of functions. In this case, when the amount of protein in a triploblastic cell derived from a stem cell and the amount of protein in a tissue structure are measured, the ten or more types of proteins include all proteins whose amounts in the tissue structure vary by 20% or more relative to the amount of protein in the triploblastic cell derived from the stem cell.

The plurality of functions are not limited to the above-mentioned specific examples. Any function or element may be used as the plurality of functions, as long as the amount or size of the functions can be measured by an arbitrary device. Additionally, it is preferable that values (measured values or analytical values) obtained by measuring or analyzing the amount or size of the functions vary when an organ bud or a triploblastic cell derived from a stem cell differentiates and matures into a tissue structure. More particularly, it is preferable that the values vary by two-fold or more.

Regarding the Measurement (Detection) of the Plurality of Functions

The plurality of functions are measured by an instrument for measuring the functions to be adopted.

The gene expression level can be analyzed by, for example, a gene microarray analyzer. In the gene analysis, for example, a gene analysis method using a chip, which is introduced in the following URLs, can be used.

http://www.chem-agilent.com/contents.php?id=1002411
http://www.gelifesciences.co.jp/newsletter/biodirect_mail/technical_tips/tips21.html
(Explanation on the Principle of Microarray by GE)

The amount of protein can be measured by, for example, a protein array analyzer. Examples of the protein analysis are introduced in the following URLs.

http://www.filgen.jp/Product/Bioscience2/index.htm
http://www.filgen.jp/Product/BioScience22-MS/index2.htm Additionally, when the genes or proteins which are specifically expressed in an organ of interest are known, the expression level a specific gene or the amount of a specific protein can be analyzed to verify if the gene expression level or the amount of a protein varies by two-fold or more. It is preferable that ten or more types of characteristic functions exist in an organ of interest.

It is more preferable that a comprehensive analysis be conducted by the method described above to obtain ten or more functions that vary by two-fold or more.

In the case of a tissue structure having the characteristics of a liver tissue, all or some of the species of the genes specific for a liver tissue can be selected by using DMET (a registered trademark) Plus available from Affymetrix, Inc. In the case of a tissue structure having the characteristics of a pancreas, in particular, islet β-cells, all or some of the species of the genes or the species of the proteins that vary between fetal and adult tissues can be selected as disclosed in Non Patent Literature 4 and 5.

Measured values (analytical values) for the plurality of functions are obtained by the above-mentioned method, and an assay is carried out. As for the gene expression level used for the assay, a normalized value obtained by dividing the expression level of a selected gene by the expression level of a house keeping gene, GAPDH (glyceraldehyde-3-phosphate dehydrogenase), β-actin, β2-microglobulin, and HPRT 1 (hypoxanthine phosphoribosyltransferase 1) can be used as a measured value (analytical value). A value normalized by a method such as Shiftile method can also be used as a measured value (analytical value). Unless otherwise stated, the term "gene expression level" used herein refers to a value normalized in the manner as described above. As for the amount of protein, a value obtained by dividing the amounts of proteins of the plurality of selected functions by the amount of albumin, or a value obtained by dividing the amounts of proteins of the plurality of selected functions by the total amount of proteins can be used as a measured value.

Method of Preparing a Tissue Structure

A tissue structure is prepared by co-culturing a triploblastic cell derived from a stem cell and at least one cell and/or factor selected from the group consisting of a vascular cell, a mesenchymal cell, a factor secreted by a vascular cell, a factor secreted by a mesenchymal cell, and a factor secreted when both a vascular cell and a mesenchymal cell exist.

Specifically, the method of preparing a tissue structure according to an embodiment includes, for example, co-culturing at least two types (preferably, three types) of cells in order form differentiated cells; further causing the differentiated cells, which are formed by continuing the co-culture, to mature into a cultured form; causing the cultured form to exhibit a plurality of functions; and picking the cultured form having a plurality of functions as a tissue structure.

The term "co-culture" generally refers to mixing two or more different types of cells each other and culturing them together.

The co-culture according to the embodiment includes the steps of: forming an aggregate; co-culturing the formed aggregate and differentiating the aggregate; and further culturing the aggregate for maturation. For ease of explanation, the case of co-culturing an aggregate to form an organ bud and maturing the organ bud to thereby prepare a tissue structure is illustrated below. However, as described above, a differentiated cell is not limited to an organ bud, but instead may also include a cell or tissue formed by differentiating an aggregate, as a matter of course.

The co-culture described below includes the steps of: (1) forming an aggregate; (2) forming an organ bud; and (3) culturing the organ bud for maturing.

The steps will be described below.

(1) Step of Forming an Aggregate (Aggregate Forming Step)

In the step of forming an aggregate, an aggregate used as a triploblastic cell derived from a stem cell is formed.

As methods for forming an aggregate, various methods are known, such as a hanging drop method in which a spheroid is formed in a droplet; a method using a chamber having a concave and convex pattern of a mesh structure or a nano-order pillar structure on the bottom surface of the culture chamber; a method of forming a spheroid in a state where cells are suspended in a medium while agitating the medium in a roller bottle; a method of culturing on a gel such as agarose or matrigel; and a method of forming a spheroid by using a culture chamber which is subjected to a cell non-adhesive treatment and is placed in a stationary state. Any one of these methods may be used in the present invention. Specific methods are introduced in various documents such as Non Patent Literature 5 and Non Patent Literature 6).

(2) Step of Forming an Organ Bud (Organ Bud Forming Step)

In the step of forming an organ bud, three types of cells, i.e., a vascular cell, a triploblastic cell derived from a stem cell, and a mesenchymal cell are co-cultured to thereby form an organ bud.

A ratio of three types of cells to be co-cultured is not particularly limited as long as the ratio is within a range in which an organ bud can be formed. The ratio of the number of the cells is preferably (a triploblastic cell derived from a stem cell):(a vascular cell):(a mesenchymal cell)=10:10-5:2-1.

Either one or both of a vascular cell and a mesenchymal cell may be substituted by substances such as a factor secreted by a vascular cell, a factor secreted by a mesenchymal cell, or a factor secreted as a result of the presence of both a vascular cell and a mesenchymal cell.

Examples of the substances such as a factor secreted by a vascular cell, a factor secreted by a mesenchymal cell, a factor secreted as a result of the presence of both a vascular cell and a mesenchymal cell, and so forth include, but are not limited to, FGF2, FGF5, BMF4, BMP6, and CTGF.

With respect to the amount of addition of these substances, FGF2 may be added at 10-100 ng/ml, preferably at about 20 ng/ml, per $1\times10^6$ cells; and BMF4 may be added at 10-100 ng/ml, preferably at about 20 ng/ml, per $1\times10^6$ cells.

The medium used for culture is not particularly limited. Any medium may be used as long as it enables the formation of a tissue structure. Preferably, a medium for culture, a medium for culture of a stem cell (for culture of an ES cell and an iPS cell), or a mixture of these two media may be used. As a medium for culturing a vascular cell, any medium may be used but, preferably, a medium containing at least one of the following substances may be used: hEGF (recombinant human epidermal growth factor), VEGF (vascular endothelial growth factor), hydrocortisone, bFGF, ascorbic acid, IGF1, FBS, antibiotics (e.g., gentamycin or amphotericin B), heparin, L-glutamine, phenolred, and BBE. Specific examples of the medium for culturing a vascular cell include EGM-2 BulletKit (manufactured by Lonza, Inc.), EGM BulletKit (manufactured by Lonza, Inc.), VascuLife EnGS Comp Kit (manufactured by LCT, Inc.), Human Endothelial-SFM Basal Growth Medium (manufactured by Invitrogen, Inc.), and human microvascular endothelial cell growth medium (manufactured by TOYOBO CO., LTD.). As a medium for culturing triploblastic cells derived from stem cells, any culture medium may be used but, when the tissue structure of interest is a liver tissue, a medium for culturing hepatocytes is preferably used. More particularly, a medium containing at least one of the following substances may be preferably used: ascorbic acid, BSA-FAF, insulin, hydrocortisone, and GA-1000. As a medium for culturing hepatocytes, commercially-available HCM BulletKit (manufactured by Lonza, Inc.) from which hEGF (recombinant human epidermal growth factor) has been removed and RPMI1640 (manufactured by Sigma-Aldrich Co.) to which 1% B27 Supplements (manufactured by GIBCO CO., LTD.) and 10 ng/mL hHGF (manufactured by Sigma-Aldrich Co.) have been added may be preferably used. More preferably, GM BulletKit (manufactured by Lonza, Inc.) and HCM BulletKit (manufactured by Lonza, Inc.) from each of which hEGF (recombinant human epidermal growth factor) has been removed are mixed at 1:1; dexamethasone, oncostatin M, and HGF are added to the resultant mixture; and the medium thus obtained may be used.

The temperature for culture is not particularly limited, but is preferably 30 to 40° C., and more preferably, 37° C.

A culture period is not particularly limited, but is preferably 3 to 50 days, and more preferably, 15 days.

(3) Step of Culturing and Maturing the Organ Bud (Maturation Step)

In the maturation step, a cultured form (a tissue structure candidate, which refers to a cultured form cultured in a chamber for preparing a tissue structure described below) is formed by maturing the formed organ bud. In other words, a cultured form is formed and the cultured form that is determined to be appropriate (i.e., satisfies the requirements) as a result of assaying the plurality of functions of the cultured form is used as a tissue structure.

For example, a culture chamber (test chamber) having the same size as that of the culture chamber (chamber for preparing a tissue structure) used for forming a tissue structure is prepared, and another culture chamber (test chamber) that is smaller or larger than the culture chamber is also prepared. The composition of the medium, the seeding density, the frequency of medium replacement, and the ratio between the cells and the amount of medium in the case of culture in the test chamber are the same as those in the case of culture in the chamber for preparing a tissue structure. The gene expression level is measured using the cultured form prepared in the test chamber. The gene expression levels of ten or more types of genes are used as the plurality of functions, and genes whose gene expression levels in the tissue structure vary by two-fold or more relative to those gene expression levels of a triploblastic cell derived from a stem cell are picked as the ten or more types of genes.

As for the picked species of the genes, the gene expression levels of the cultured form prepared in the test chamber, a cells or biological tissue sampled from a fetus, and a cell or biological tissue sampled from an adult are measured, and are used for determination. In other words, the results of the determination of the cultured form cultured in the test chamber can be replaced by the determination results of the cultured form prepared in the chamber for preparing a tissue structure.

The above case assumes that a cell stack or a flask is used as the chamber for preparing a tissue structure and a dish or a small flask (24 cm$^2$) is used as the test chamber. In the case of using a well plate, different wells can be treated as test chambers (or test wells).

In the maturation step, a medium for culturing a desired tissue is preferably used as the medium, and it is preferable to mix a medium for a vascular cell and a medium for a stem cell.

(4) Regarding Determination Method

The determination method is a method of evaluating the similarity of a tissue structure to an adult, and the tissue structure is premised on functions similar to those of the adult. Accordingly, the gene expression level of a cell or biological tissue sampled from an adult and the gene expression level of a tissue structure show a positive correlation. If the gene expression levels show a negative correlation, it is determined that maturation is insufficient and the functions are not close to those of an adult. That is, it is necessary that the gene expression level of a cell or biological tissue sampled from an adult and the gene expression level of a tissue structure show a positive correlation. If correlation coefficients [a] and [b], which are defined as described below, have a relationship that [a] is smaller than [b] and [b] is smaller than "1" (in other words, a relationship that satisfies [a]<[b]<1), the tissue structure candidate is determined to be a tissue structure.

[a]: A positive correlation coefficient between "the gene expression level of a cell or biological tissue sampled from a living body" and "the gene expression level of a cultured form (test chamber)"; and a correlation coefficient between "the gene expression level of a cell or biological tissue sampled from a fetus" and "the gene expression level of a cultured form (test chamber)".

[b]: A correlation coefficient between "the gene expression level of a cell or biological tissue sampled from a living body" and "the gene expression level of a cultured form (test chamber)"

As a method of calculating a Pearson correlation coefficient, it is preferable to use software for informatics to effectively perform an operation (for example, assuming a case where several hundreds of genes are assayed). As the software, for example, Gene Spring or Subio is preferably used. As another alternative, Excel software available from Microsoft Corporation may be used for the assay.

In the organ bud forming step and the maturation step, an aggregate (spheroid) is cultured using culture chambers. Also in the aggregate forming step, culture chambers may be used. Culture chambers may be used in all the steps of culturing and maturing cells.

In the aggregate forming step, the organ bud forming step, and the maturation step, it is preferable that cells are being combined to form an aggregate. In the aggregate forming step, the organ bud forming step, and the maturation step, it is preferable that cells are being combined to form a cell cluster having a spheroid shape. Additionally, it is preferable that the diameter of the spheroid formed by the cells is in a range from 50 μm to 2 mm.

A culture chamber having the following structure, for example, is used.

<Culture Chamber>

FIG. 1 is a diagram showing an example of a culture chamber according to an embodiment. FIG. 1 shows a part of a culture plate 3 including a plurality of culture chambers 1. The upper part of FIG. 1 shows some of a plurality of recesses 10 which are formed in the bottom of each of the culture chambers 1, when viewed from the top of the culture plate 3. The plurality of recesses 10 are arranged in each of the culture chambers 1. In terms of the production of the culture chambers 1 and the efficiency of cell culture, it is preferable to arrange the plurality of recesses 10 in a regular manner. One culture chamber 1 corresponds to, for example, one well arranged in a plate including a plurality of wells. In other words, the plurality of recesses 10 are arranged in the respective wells of a well plate.

A well plate is an experimental/testing instrument formed of a flat plate having a number of dents (holes or wells), and each well is used as a test tube or a petri dish. The number of wells is, for example, 6, 24, 96, 384, or more. Examples of the shape of the bottom of each well include a flat shape, a round shape, and a combination of a number of elongated microtubes (deep well plate).

Figure 2:
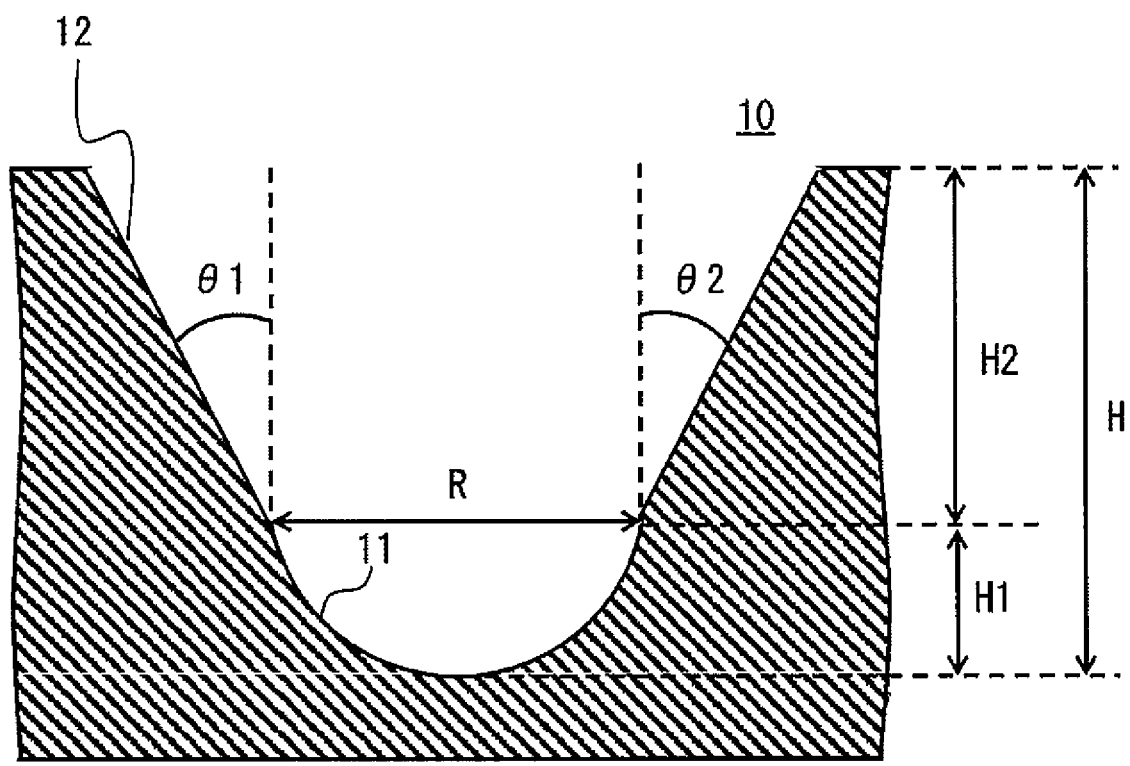
FIG. 2 is a cross-sectional view showing an example of the shape of a recess according to the embodiment.
Figure 3:
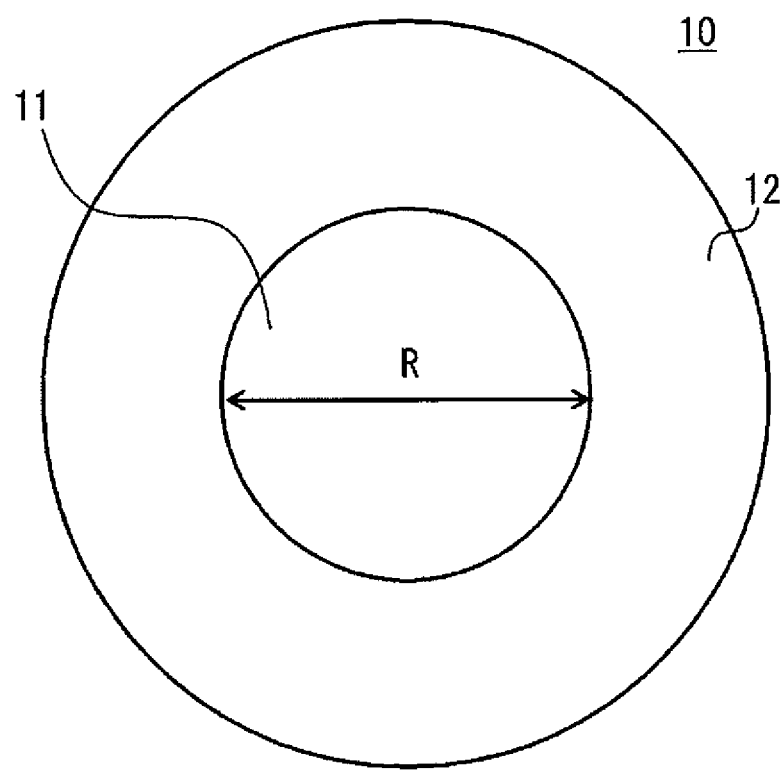
FIG. 3 is a top view showing an example of the shape of the recess according to the embodiment.

FIGS. 2 and 3 show an example of the shape of each recess according to a first embodiment. FIG. 2 shows a cross-sectional view of one recess 10 as viewed from the side, and FIG. 3 shows a top view of one recess 10.

Each recess 10 is composed of a bottom portion 11 and an opening 12. The bottom portion 11 is a portion serving as the bottom of the culture chamber 1, and the opening 12 is a portion disposed above the bottom portion 11. A portion where the bottom portion 11 and the opening 12 are in contact is referred to as a boundary. In FIG. 2, a portion whose length is indicated by an arrow "R" corresponds to the location of the boundary. In FIG. 3, the boundary location is indicated by a double dashed chain line. Note that the bottom portion 11 and the opening 12 are formed of a continuous surface and are produced in an integrated manner.

FIGS. 2 and 3 show an equivalent diameter R and a depth (height) H of each of the plurality of recesses 10 formed in the culture chamber 1.

The term "equivalent diameter R" refers to the diameter of a circle inscribed in the bottom portion 11 of each recess 10. In this case, the equivalent diameter R is the diameter of an inscribed circle that is inscribed at the boundary between the bottom portion 11 and the opening 12. More specifically, the equivalent diameter R is the diameter of a circle inscribed in a shape of a plane that is perpendicular to the direction of the height H of each recess 10 at the boundary.

The term "depth H" refers to a length from the bottom on the inside of the bottom portion 11 to an upper end of each recess 10. The upper end of the recess 10 corresponds to an end (upper end) of the opening 12. The depth H corresponds to the depth of a space formed by the recess 10. In other words, the depth H is a depth from the bottom of a space, which is formed by the bottom portion 11, to an upper end of a space formed by the opening 12. FIG. 2 shows not only the depth H of the recess 10, but also a depth H1 of the bottom portion 11 and a depth H2 of the opening 12.

The bottom portion 11 forms a space (first space) in which cells are cultured. The bottom portion 11 has, for example, a hemispherical shape. For example, a shape obtained by dividing a spherical shape having the equivalent diameter R as a diameter into halves can be used. The shape of the bottom portion 11 is not limited to a hemispherical shape.

The opening 12 forms a space (second space) that operates to support culture and collection of cells. The opening 12 is formed of a wall which surrounds an area from a boundary between the opening 12 and the bottom portion 11 to an end (tip) of the recess 10 and which has a taper angle in a range from 1 degree to 20 degrees. The taper angle of the wall constituting the opening 12 is preferably in a range from 5 degrees to 15 degrees, and more preferably, 10 degrees. This is because if the taper angle is extremely small, it is difficult to transfer cells from the recesses into the medium during collection of the cells, and if the taper angle is extremely large, the cells are removed during replacement of the medium.

Taper angles are represented by θ1 and θ2 in FIG. 2. In an example of the shape of each recess 10 shown in FIGS. 2 and 3, the taper angles θ1 and θ2 are substantially the same.

The boundary between the bottom portion 11 and the opening 12 is formed in such a manner that the equivalent diameter R is in a range from 50 μm to 1 mm. To supply nutrients to a central portion of a spheroid, the equivalent diameter is preferably in a range from 50 μm to 500 μm, and more preferably, in a range from 100 μm to 500 μm.

Additionally, the boundary is formed in such a manner that the depth H from the bottom of the bottom portion to the end is set to be in a range from 0.5 or more times to 3 or more times the equivalent diameter R. The depth H is preferably in a range from 0.7 or more times to 1.2 or less times the equivalent diameter R, and more preferably, in a range from 0.8 times to 1 time the equivalent diameter R.

In the culture chamber, the area between two adjacent recesses 10 is preferably flat. For example, the distance between two recesses 10 is preferably in a range from 5 μm to 50 μm. This is because the area between two recesses 10 provides an effect of preventing a cell from running on the wall, adhering to the wall, and proliferating to form a spheroid on the wall. However, if the distance is small, cracking is more likely to occur due to a vibration during cell seeding or replacement of the medium. Accordingly, it is preferable that the distance between two recesses 10 is 5 μm or more. In view of this, it is preferable that the distance between two recesses 10 is in a range from 5 to 20 μm.

The culture chamber 1 having the above-described shape is preferably produced in the following manner.

The culture chamber 1 is preferably a resin molding formed of one or a combination of two or more selected from the group consisting of acrylic resin, polylactic acid, polyglycolic acid, styrene resin, acrylic styrene copolymer resin, polycarbonate resin, polyester resin, polyvinyl alcohol resin, ethylene vinyl alcohol copolymer resin, thermoplastic elastomer, vinyl chloride resin, and silicon resin.

It is preferable that a functional group is formed on the surface of each recess 10 of the culture chamber 1 by a surface modification treatment method of any one of plasma treatment, glass coating, corona discharge, and UV ozonation, or a combination thereof and the treatment is performed so that the water contact angle becomes 45 degrees or less.

Additionally, it is preferable that a hydrophilic polymer chain that inhibits cell adhesion is immobilized on the recesses 10. More preferably, a hydrophilic polymer chain is immobilized on the surface of each recess 10 that is treated so that the water contact angle becomes 45 degrees or less as mentioned above.

Furthermore, it is preferable that a phospholipid or a phospholipid-polymer complex is immobilized on the surface of each recess 10. More preferably, this immobilization treatment is performed on each recess 10 that is treated so that the water contact angle becomes 45 degrees or less, each recess 10 on which a hydrophilic polymer chain is immobilized, or a combination of these recesses 10.

Further, it is preferable that the recesses 10 have a cell non-adhesive surface on which at least one polymer of a hydrophilic polymer chain that inhibits cell adhesion, and a phospholipid, or a phospholipid-polymer complex is immobilized after a functional group is formed on the surface of each recess 10 by a surface modification treatment method of any one of plasma treatment, glass coating, corona discharge, and UV ozonation, or a combination thereof and the treatment is performed so that the water contact angle becomes 45 degrees or less. This treatment is preferably carried out together with each of the above-mentioned treatments, or a combination of the treatments.

Poly(hydroxyethyl methacrylate) is preferably used as the above-mentioned hydrophilic polymer chain. More preferably, the average molecular weight of poly(hydroxyethyl methacrylate) is 100,000 or more.

Figure 4:
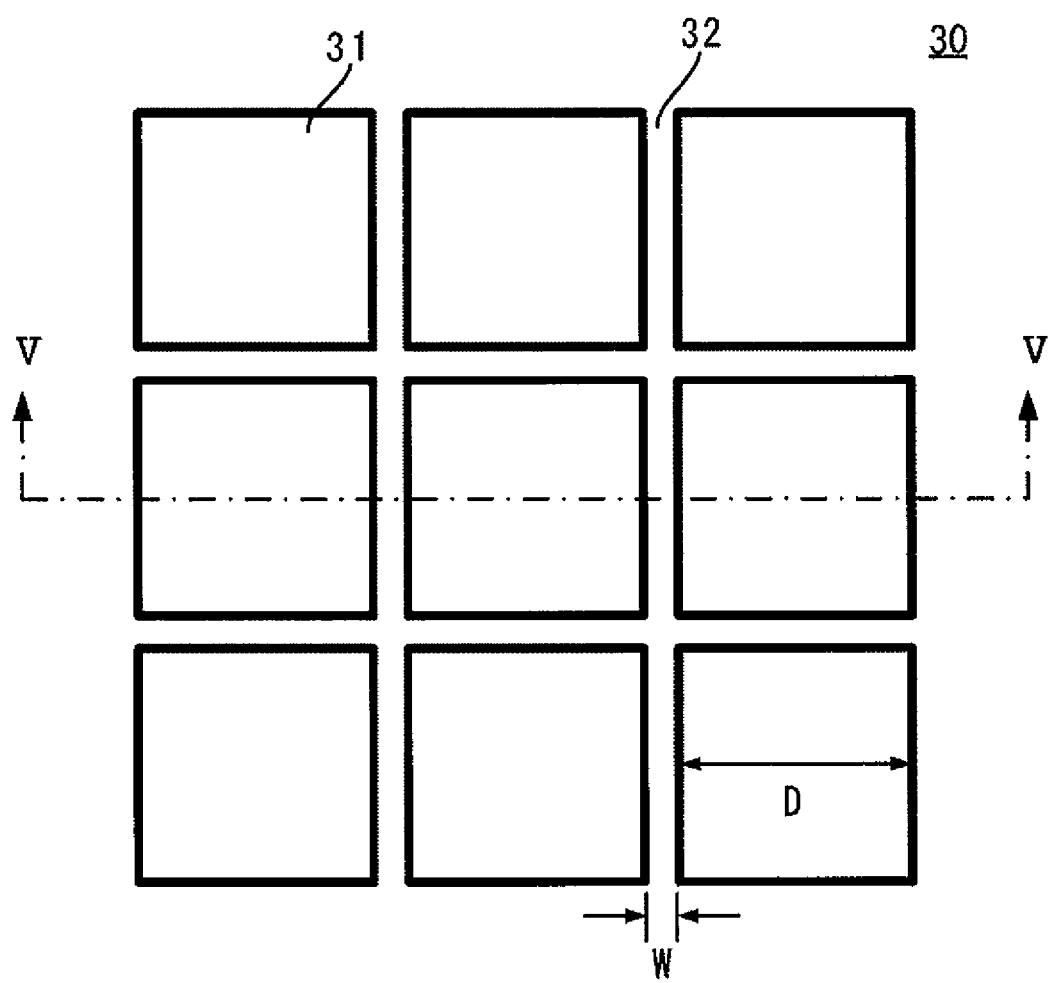
FIG. 4 is a diagram showing another example of the shape of the culture chamber.
Figure 5:
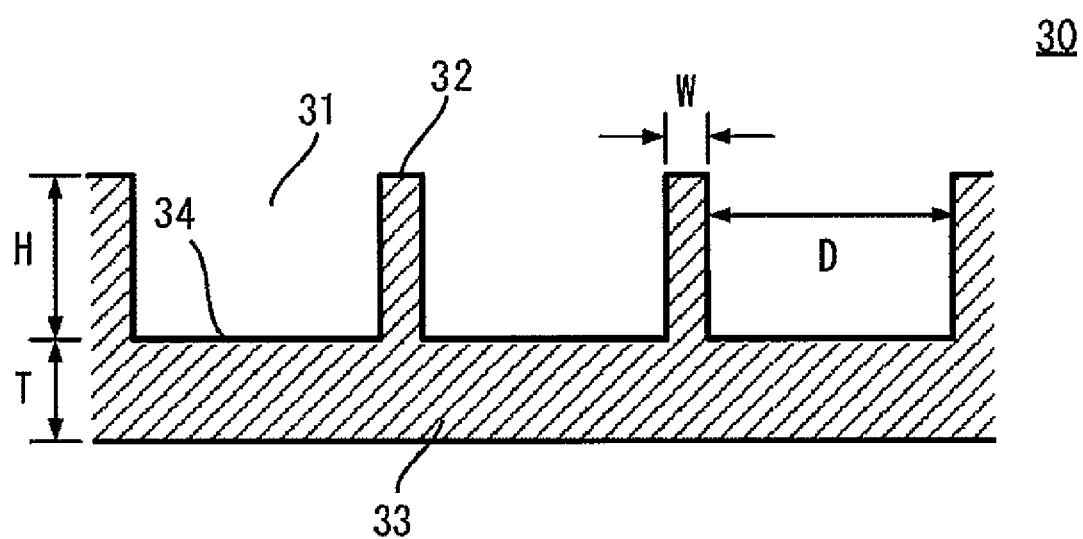
FIG. 5 is a sectional view of the culture chamber taken along a line V-V of FIG. 4.

As the culture chamber 1, not only the culture chambers shown in FIGS. 1 to 3, but also culture chambers in which micropatterns shown in FIGS. 4 and 5 are formed can be used.

FIG. 4 shows another example of the shape of the culture chamber used in an embodiment. FIG. 5 is a sectional view of the culture chamber taken along a line V-V of FIG. 4.

A culture chamber 30 includes culture spaces 31, walls 32, and a bottom portion 33.

Each culture space 31 is an area partitioned by the walls 32 and the bottom portion 33, and serves as a three-dimensional space area (culture area) in which cells are cultured. The culture space 31 is also referred to as simply "space" or "micro-space".

The walls 32 are partition walls that partition the culture spaces 31. It can also be said that each of the walls 32 is a convex portion that forms a concave and convex pattern in the culture chamber 30.

The bottom portion 33 functions as a substrate for the culture chamber 30, and the surface of the bottom portion 33 on which the culture space 31 is formed is a part of the culture area (culture surface). The bottom portion 33 has the same area as that of the bottom of each well formed in the culture plate shown in FIG. 1, for example, and the bottom of each well is used as the bottom portion 33. The bottom portion 33 forms the bottom of each culture space 31. The surface of the bottom portion 33 that is a part of the surface forming the culture space 31 and serves as the culture area is referred to as "a bottom culture surface 34".

As for each culture space 31 formed in the culture chamber 30, FIGS. 4 and 5 show an equivalent diameter D, the height (depth) H, a width (thickness) W of each of the walls 32, and a thickness T of the bottom portion 33. FIGS. 4 and 5 show a case where the bottom portion 33 is produced integrally with the walls 32.

The term "equivalent diameter D" refers to the diameter of a circle inscribed in each culture space 31, like the equivalent diameter R shown in FIG. 2. More specifically, the equivalent diameter D is the diameter of a circle inscribed in the shape of a face (shape of a front face) parallel to the bottom portion 33 of each culture space 31, that is, the shape of a face perpendicular to the direction of the height H of each culture space 31. When the shape of the front face of each culture space 31 varies depending on the height H, a maximum value of a space area in which an established hepatic cell line is cultured is defined as the equivalent diameter.

The height H is the length from the bottom (bottom culture surface 34) of the culture space 31 to the upper surface of each wall 32. It can also be said that the height H is the depth of each culture space 31. When the bottom culture surface 34 is a flat surface, the height H is the same as the height of each wall 32.

The width W of each wall 32 is the thickness of each wall 32. It can also be said that the width W is the distance between two adjacent culture spaces 31.

In the culture chamber 30 (in other words, in each well), the plurality of culture spaces 31 are arranged in an array as shown in FIG. 4. The number or size of the culture spaces 31 included in the culture chamber 30 depend on the number of wells (the size of wells), which are formed in the culture plate, and on the size of each of the culture spaces 31 and the walls 32. FIGS. 4 and 5 show nine culture spaces 31. These are illustrated for ease of explanation, and thus the number of culture spaces 31 does not correspond to the actual number of culture spaces 31 included in the culture chamber 30 (each well).

Figure 6:
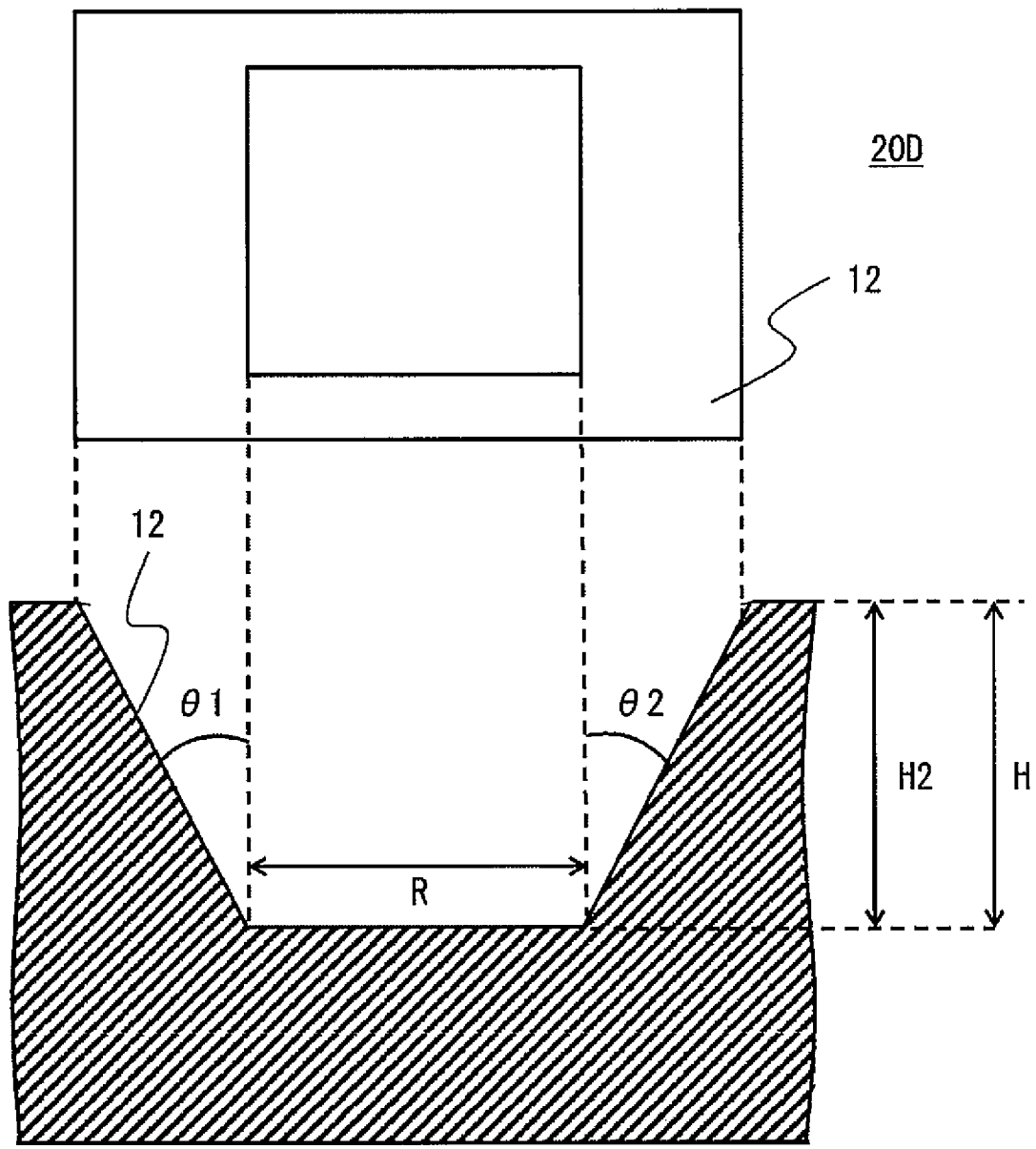
FIG. 6 is a diagram showing still another example of the shape of the culture chamber.

A recess 20D shown in FIG. 6 may also be used as a culture chamber. FIG. 6 shows an example of the shape of the recess 20D having a linear bottom portion, in other words, a bottom portion that provides no space. The upper part of FIG. 6 shows an elevational view of the recess 20D as viewed from the top, and the lower part of FIG. 6 shows a sectional view of the recess 20D. The recess 20D is formed of the opening 12.

Aggregates are co-cultured in the recesses 10 of the culture chamber 1 described above. Each recess 10 is also referred to as a microchamber.

In addition to the features described above, the recesses 10 are preferably formed in the following manner.

Each recess 10 preferably has an equivalent diameter in a range from 20 μm to 2.5 mm and a depth in a range from 20 μm to 2.5 mm.

A tissue structure is preferably cultured using a culture chamber including a culture surface which is a cell non-adhesive surface.

It is preferable that the culture surface of the culture chamber 11 is coated with a polymer selected from the group consisting of a phospholipid, a phospholipid-polymer complex, poly(2-hydroxyethyl methacrylate) (PHEMA), poly-vinyl alcohol, agarose, chitosan, polyethyleneglycol, and albumin, or a combination thereof, the culture surface being a surface in contact with cells.

A vascular cell, an endodermal, ectodermal, or mesodermal cell derived from a stem cell, and a mesenchymal cell are preferably co-cultured at a ratio of 10:7-10:1-2, and cells are preferably seeded at a density of 20 to 2000 cells per recess 10 (per microchamber). Each recess 10 is preferably composed of the bottom portion 11 and the opening 12.

The opening 12 is preferably defined by a wall which surrounds an area from a boundary between the opening and the bottom to the end and which has a taper angle in a range from 1 degree to 20 degrees. The bottom portion 11 preferably has one of a hemispherical shape and a truncated cone shape.

The tissue structure prepared as described above can be used for, for example, drug discovery screening and regenerative medicine.

The present invention also provides a method of evaluating a drug using the tissue structure prepared in the manner as described above. Examples of the drug evaluation include prediction of drug metabolism profiles of candidate compounds for drugs, drug efficacy evaluation, toxicity evaluation, and evaluation of drug interactions.

EXAMPLES

Experimental Method (1) Preparation of a Triploblastic Cell Derived from a Stem Cell A human iPS cell (human skin-derived TkDA3 hiPSC clone (provided by Mr. Koji Eto and Mr. Hiromitsu Nakauchi)) was cultured in an activin-supplemented serum-free medium to thereby induce CXCR4− and E-cadherin-positive an endodermal cell. The resultant endodermal cell was cultured in the presence of added BMP4 and FGF2 for two days to thereby obtain a CXCR4-negative and HNF4α-positive hepatic endoderm cell population. Expressions of CXCR4 and HNF4α were confirmed by immunostaining and gene expression analysis in accordance with the descriptions in Hepatology, 51(1), 297-305, 2010.

(2) Preparation of a Tissue Structure

Cell seeding ratio: The resultant hepatic endoderm cell, vascular endothelial cell (human umbilical cord blood-derived vein endothelial cells) (Lonza, Basel, Switzerland), and undifferentiated mesenchymal cell (human mesenchymal stem cells) (Lonza, Basel, Switzerland) were mixed at a ratio of 10:5-10:2, to thereby prepare a cell solution. The vascular endothelial cell and the undifferentiated mesenchymal cell which were individually labeled with fluorescence in advance were used.

Medium: Endothelial cell medium kit-2: EGM-2 Bullet-Kit (product code CC-3162: Lonza) or endothelial cell medium kit: EGM BulletKit (product code CC-3124: Lonza) was used.

Culture method: The above-mentioned cell solution and medium were used for both an example and a comparative example.

Example

Referring to FIGS. 1 to 3, a 24-well plate including recesses (spaces) having an equivalent diameter of 500 μm and a depth of 500 μm was used as a culture chamber. To suppress the cell adhesion properties, p-HEMA was coated on a culture surface in contact with a cell.

After culture for 3 to 15 days, an aggregate was formed. On the 15th day of the culture, the aggregate (cultured form) was collected and a gene expression analysis was conducted. At this time, the size of the aggregate was 2 mm or less.

Comparative Example

A matrigel-coated φ3 cm dish was used.

Cell suspension was seeded onto a solidified matrigel (BD pharmingen), which was a stock gel or two-fold dilution, in the culture dish.

After culture for 3 to 15 days, an aggregate was formed. If the size of the aggregate is increased to 2 mm or more, nutrients are not supplied to the center portion of the aggregate, so that the cells become necrotic. Accordingly, the culture was terminated at the time the diameter of the aggregate became 2 mm. A gene expression analysis was conducted on the cultured form thus prepared.

(3) Assay of the Plurality of Functions

1. Selection of Values of the Plurality of Functions

An comprehensive analysis was conducted on the gene expression levels of an iPS cell obtained from a cell bank, a hepatocyte derived from a 10-week-old fetus, and a hepatocyte derived from a 30-year-old adult, by using GeneChip (Agilent Technologies Co., Ltd.; Whole Human Genome DNA Microarray 4x44K v2 G4845A) (hereinafter, the value of the gene expression level of hepatocytes derived from an adult is referred to as "value B", and the value of the gene expression level of hepatocytes derived from a fetus is referred to as "value C"). Seventy genes were picked as the species of the genes that are expressed in a human body whose gene expression level increases as the maturation advances (an iPS cell→a hepatocyte derived from the fetus→a hepatocyte derived from the adult) (Tables 1-1 to 1-3). Further, the gene expression level (value A) of a liver bud, which was prepared according to Patent Literature 3, and the gene expression level (value D) of a tissue structure according to the example were calculated. The species of the genes in which the value D increased by two-fold or more relative to the value A, the species of the genes in which the value D increased by more than ten-fold relative to the value A, and the species of the genes in which the value D increased by more than 100-fold relative to the value A were picked (Table 2-1, Table 2-2). There were 49 species of the genes in which the value D increased by more than ten-fold relative to the value A. There were 61 species of the genes in which the value D increased by two-fold or more relative to the value A. There were 38 species of the genes in which the value D increased by more than 100-fold relative to the value A.

TABLE 1-1

| GeneSymbol | GeneName |
|---|---|
| IL13RA1 | interleukin 13 receptor, alpha 1 |
| IFIT1 | interferon-induced protein with tetratricopeptide repeats 1 |
| KLF9 | Kruppel-like factor 9 |
| SORD | sorbitol dehydrogenase |
| ALDOB | aldolase B, fructose-bisphosphate |
| TNFSF10 | tumor necrosis factor (ligand) superfamily, member 10 |
| APOC3 | apolipoprotein C-III |
| UBD | ubiquitin D |
| RBP1 | fructose-1,6-bisphosphatase 1 |
| FGGY | FGGY carbohydrate kinase domain containing |
| PNPLA7 | patatin-like phospholipase domain containing 7 |
| SERPING1 | serpin peptidase inhibitor, clade G (C1 inhibitor), member 1 |
| ABCA6 | ATP-binding cassette, sub-family A (ABC1), member 6 |
| PNPLA7 | patatin-like phospholipase domain containing 7 |
| NFIC | nuclear factor I/C (CCAAT-binding transcription factor) |
| ALDOB | aldolase B, fructose-bisphosphate |
| ETFDH | electron-transferring-flavoprotein dehydrogenase |

TABLE 1-1-continued

| GeneSymbol | GeneName |
|---|---|
| IL13RA1 | interleukin 13 receptor, alpha 1 |
| ABCC3 | ATP-binding cassette, sub-family C (CFTR/MRP), member 3 |
| ACAT1 | acetyl-CoA acetyltransferase 1 |
| SERPING1 | serpin peptidase inhibitor, clade G (C1 inhibitor), member 1 |

TABLE 1-2

| GeneSymbol | GeneName |
|---|---|
| TNFSF10 | tumor necrosis factor (ligand) superfamily, member 10 |
| PXMP2 | peroxisomal membrane protein 2, 22 kDa |
| MAT1A | methinonine adenosyltransferase I, alpha |
| ITIH4 | inter-alpha (globulin) inhibitor H4 (plasma kallikrein-sensitive glycoprotein) |
| SERPING1 | serpin peptidase inhibitor, clade G (C1 inhibitor), member 1 |
| CTSO | cathepsin O |
| SERPING1 | serpin peptidase inhibitor, clade G (C1 inhibitor), member 1 |
| LRG1 | leucine-rich alpha-2-glycoprotein 1 |
| CLDN2 | claudin 2 |
| KNG1 | kininogen 1 |
| C3 | complement component 3 |
| TDO2 | tryptophan 2,3-dioxygenase |
| ORM1 | orosomucoid 1 |
| G0S2 | G0/G1switch 2 |
| DEFB1 | defensin, beta 1 |
| ALDH3A2 | aldehyde dehydrogenase 3 family, member A2 |
| MGLL | monoglyceride lipase |
| PSMB9 | proteasome (prosome, macropain) subunit, beta type, 9 (large multifunctional peptidase 2) |
| HAMP | hepcidin antimicrobial peptide |
| ACAT1 | acetyl-CoA acetyltransferase 1 |
| HGD | homogentisate 1,2-dioxygenase |
| MX1 | myxovirus (influenza virus) resistance 1, interferon-inducible protein p78 (mouse) |
| ABCC3 | ATP-binding cassette, sub-family C (CFTR/MRP), member 3 |

TABLE 1-3

| GeneSymbol | GeneName |
|---|---|
| CFH | complement factor H |
| MGLL | monoglyceride lipase |
| C3 | complement component 3 |
| VKORC1 | vitamin K epoxide reductase complex, subunit 1 |
| CFI | complement factor I |
| F12 | coagulation factor XII (Hageman factor) |
| PXMP2 | peroxisomal membrane protein 2, 22 kDa |
| PSMB8 | proteasome (prosome, macropain) subunit, beta type, 8 (large multifunctional peptidase 7) |
| CFH | complement factor H |
| CFB | complement factor B |
| ACAT1 | acetyl-CoA acetyltransferase 1 |
| CFH | complement factor H |
| SORD | sorbitol dehydrogenase |
| HP | haptoglobin |
| IGFBP4 | insulin-like growth factor binding protein 4 |
| HRG | histidine-rich glycoprotein |
| NFIC | nuclear factor I/C (CCAAT-binding transcription factor) |
| PLG | plasminogen |
| ORM2 | orosomucoid 2 |
| ALDH3A2 | aldehyde dehydrogenase 3 family, member A2 |
| TAP1 | transporter 1, ATP-binding cassette, sub-family B (MDR/TAP) |
| CFI | complement factor I |
| VKORC1 | vitamin K epoxide reductase complex, subunit 1 |
| VKORC1 | vitamin K epoxide reductase complex, subunit 1 |
| ANG | angiogenin, ribonuclease, RNase A family, 5 |
| HSD3B7 | hydroxy-delta-5-steroid dehydrogenase, 3 beta- and steroid delta- isomerase 7 |

TABLE 2-1

| | Variation Factor | | |
|---|---|---|---|
| | ×2 | ×10 | ×100 |
| Gene Number | 61 genes | 49 genes | 38 genes |
| Gene Name | VKORC1 | VKORC1 | UBD |
| | UBD | UBD | TNFSF10 |
| | TNFSF10 | TNFSF10 | TDO2 |
| | TDO2 | TDO2 | TAP1 |
| | TAP1 | TAP1 | SORD |
| | STARD10 | SORD | SERPING1 |
| | SORD | SERPING1 | PSMB9 |
| | SMPDL3A | PXMP2 | PSMB8 |
| | SERPING1 | PSMB9 | PNPLA7 |
| | SARDH | PSMB8 | PLG |
| | RGN | PNPLA7 | ORM2 |
| | PXMP2 | PLG | ORM1 |
| | PSMB9 | ORM2 | NFIC |
| | PSMB8 | ORM1 | MX1 |
| | PNPLA7 | NFIC | MGLL |
| | PLG | MX1 | LRG1 |
| | ORM2 | MGLL | KNG1 |
| | ORM1 | MAT1A | KLF9 |
| | NFIC | LRG1 | ITIH4 |
| | MX1 | KNG1 | IGFBP4 |
| | MGLL | KLF9 | IFIT1 |
| | MAT1A | ITIH4 | HSD3B7 |
| | MAGIX | IL13RA1 | HP |
| | LRG1 | IGFBP4 | HGD |
| | KNG1 | IFIT1 | G0S2 |
| | KLF9 | HSD3B7 | FBP1 |
| | ITIH4 | HRG | F12 |
| | IL13RA1 | HP | DEFB1 |
| | IGFBP4 | HGD | CTSO |
| | IFIT1 | HAMP | CLDN2 |

TABLE 2-2

| | Variation Factor | | |
|---|---|---|---|
| | ×2 | ×10 | ×100 |
| Gene Number | 61 genes | 49 genes | 38 genes |
| Gene Name | HSD3B7 | G0S2 | CFI |
| | HRG | FGGY | CFH |
| | HP | FBP1 | CFB |
| | HGB | F12 | C3 |
| | HAMP | ETFDH | APOC3 |
| | HAAO | DFFB1 | ALDOB |
| | G0S2 | CTSO | ABCC3 |
| | FTCD | CLDN2 | ABCA6 |
| | FGGY | CFI | |
| | FBP1 | CFH | |
| | F12 | CFB | |
| | ETFDH | C3 | |
| | ENTPD8 | APOC3 | |
| | DHRS1 | ANG | |
| | DEFB1 | ALDOB | |
| | CTSO | ALDH3A2 | |
| | CLDN2 | ACAT1 | |
| | CFI | ABCC3 | |
| | CFH | ABCA6 | |
| | CFB | | |
| | CES2 | | |
| | C3 | | |
| | APOC3 | | |
| | ANG | | |
| | ALDOB | | |
| | ALDH3A2 | | |
| | ALAS1 | | |
| | ACOX1 | | |
| | ACAT1 | | |
| | ABCC3 | | |
| | ABCA6 | | |

2. Calculation of Gene Expression Levels of Hepatocytes Derived from an Adult

The values used in the section of "1. Selection of values of the plurality of functions" were used as the values A, B, C, and D. Various gene expression levels were measured in the comparative example (value E). The term "gene expression level" used herein refers to a normalized value which is obtained by correcting the array results (all probe values) obtained from samples with a 75% shiftile value (75 percentile value).

Figure 7:
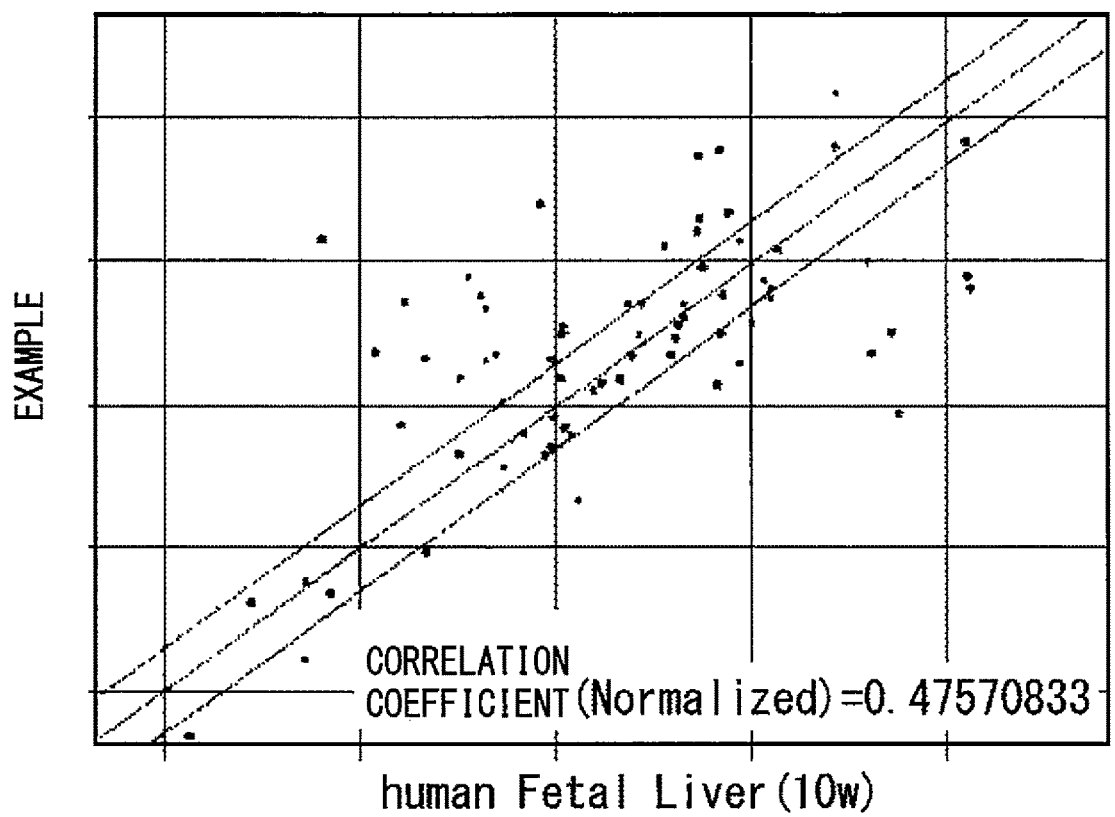
FIG. 7 is a graph showing results (scatter diagram) according to an example.
Figure 7:
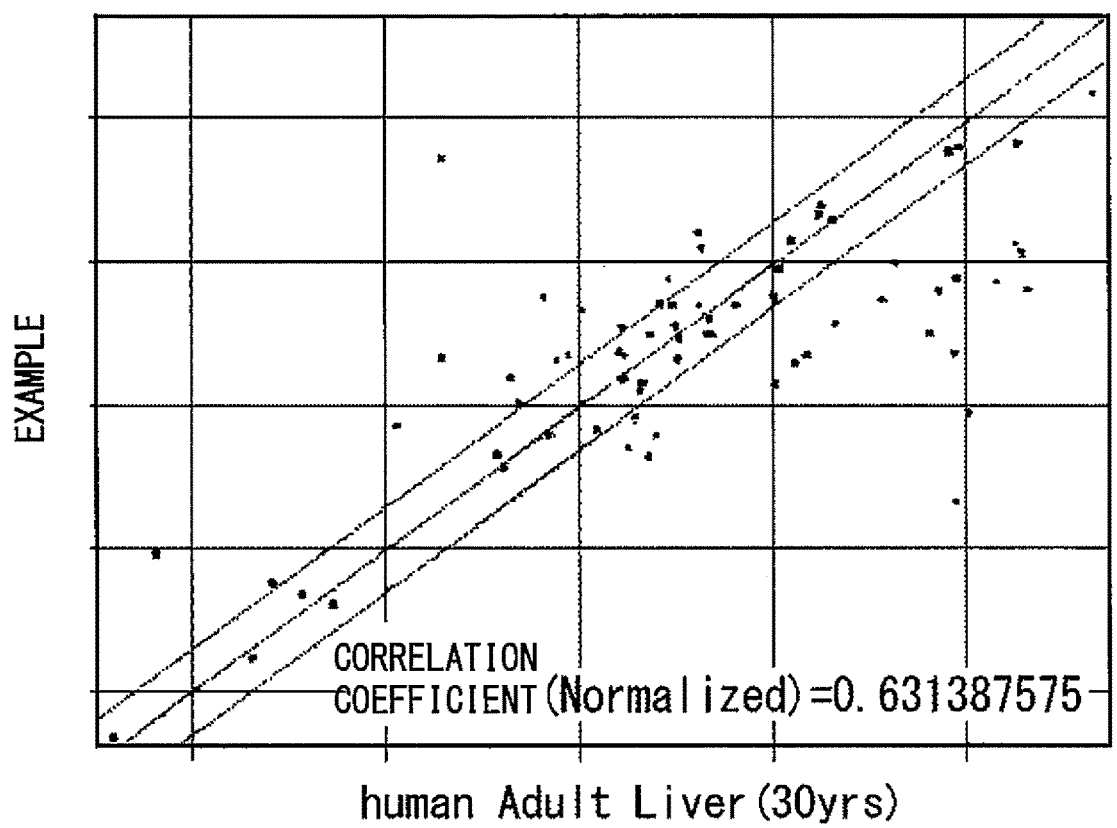

FIG. 7 shows some of the values of the gene expression levels of 49 genes of the hepatocyte derived from a living body and the hepatocyte derived from a fetus in both the example and the comparative example.

Assay

Various gene expression levels were calculated for 49 genes shown in Tables 1-1 to 1-3, and the Pearson product-moment correlation coefficient was calculated by Gene Spring.

(4) Results

Example

Genes that Vary by More than Ten-Fold: 49 Genes

The correlation coefficient between (value C) and (value D) was 0.4757.

The correlation coefficient between (value B) and (value D) was 0.6314.

FIG. 7 shows a scatter diagram.

Since the correlation coefficient for the value B regarding hepatocytes derived from the adult was closer to "1" than the correlation coefficient for the value C, the tissue structure candidate was determined to be a tissue structure.

Comparative Example

Genes that Vary by More than 10-Fold: 49 Genes

The correlation coefficient between (value C) and (value E) was −0.5000.

The correlation coefficient between (value B) and (value E) was −0.3496.

The correlation coefficient between the gene expression level (value B) of cells sampled from a living body and the gene expression level of the comparative example showed a negative correlation. Accordingly, the requirement of "positive correlation" was not satisfied, so that the tissue structure candidate was not determined to be a tissue structure.

This application is based upon and claims the benefit of priority from Japanese patent application No. 2013-122190, filed on Jun. 10, 2013, the disclosure of which is incorporated herein in its entirety by reference.

REFERENCE SIGNS LIST

1, 30 CULTURE CHAMBER
3 CULTURE PLATE
10, 20D RECESS
11 BOTTOM PORTION
12 OPENING
31 CULTURE SPACE
32 WALL
33 BOTTOM PORTION
34 BOTTOM CULTURE SURFACE

The invention claimed is:

1. A method of preparing a tissue structure, the method comprising:
co-culturing a hepatic endoderm cell with a vascular cell and a mesenchymal cell in a microchamber having an equivalent diameter of from 20 μm to 2.5 mm and a depth of from 20 μm to 1000 μm, whereby the hepatic endoderm cell, the vascular cell, and the mesenchymal cell differentiate and mature during the co-culturing to form the tissue structure, wherein the hepatic endoderm cell is obtained by inducing a stem cell in advance;
determining expression levels of genes in the tissue structure, in a biological tissue sampled from an adult, and a biological tissue sampled from a fetus; and
determining a Pearson product-moment correlation coefficient between the expression levels of the genes in the tissue structure and the expression levels of the genes in the biological tissue sampled from the adult and a Pearson product-moment correlation coefficient between the expression levels of the genes in the tissue structure and the expression levels of the genes in the biological tissue sampled from the fetus, wherein:
the Pearson-product moment correlation coefficient between the expression levels of the genes in the tissue structure and the expression levels of the genes in the biological tissue sampled from the adult is a positive value and is greater than the Pearson product-moment correlation coefficient between the expression levels of the genes in the tissue structure and the expression levels of the genes in the biological tissue sampled from the fetus; and
the genes consist of one or more of VKORC1, UBD, TNFSF10, TDO2, TAP1, SORD, SERPING1, PXMP2, PSMB9, PSMB8, PNPLA7, PLG, ORM2, ORM1, NFIC, MX1, MGLL, MAT1A, LRG1, KNG1, KLF9, ITIH4, IL13RA1, IGFBP4, IFIT1, HSD3B7, HRG, HP, HGD, HAMP, G0S2, FGGY, FBP1, F12, ETFDH, DEFB1, CTSO, CLDN2, CFI, CFH, CFB, C3, APOC3, ANG, ALDOB, ALDH3A2, ACAT1, ABCC3, ABCA6, STARD10, SMPDL3A, SARDH, RGN, MAGIX, HAAO, FTCD, ENTPD8, DHRS1, CES2, ALAS1, and ACOX1.

2. The method of claim 1, wherein the expression levels of the genes in the tissue structure, in the biological tissue sampled from the adult, and the biological tissue sampled from the fetus are analyzed by using a DNA chip on which segments of the genes are immobilized.

3. The method of claim 1, wherein the co-culturing comprises:
forming an aggregate of the hepatic endoderm cell, the vascular cell, and the mesenchymal cell;
forming an organ bud from the aggregate; and
further culturing the organ bud for maturation.

4. The method of claim 3, wherein the forming of an organ bud and the further culturing are performed such that cells in the organ bud remain aggregated.

5. The method of claim 3, wherein the forming of an aggregate is performed such that the aggregate forms a cluster having a spheroid shape, and the forming of an organ bud and the further culturing are performed such that the spheroid shape is maintained.

6. The method of claim 5, wherein the spheroid shape has a diameter in a range from 50 μm to 2 mm.

7. The method of claim 1, wherein the stem cell is a cell selected from the group consisting of a fetal stem cell and an induced pluripotent stem cell.

8. The method of claim 1, wherein the expression levels of the genes in the biological tissues sampled from the adult and the fetus are expression levels of the genes in the liver of the adult and the fetus, respectively.

9. The method of claim 1, wherein the tissue structure is cultured in a culture chamber having a culture surface which is a cell non-adhesive surface.

10. The method of claim 9, wherein the culture surface of the culture chamber is coated with a polymer selected from the group consisting of a phospholipid, a phospholipid-polymer complex, poly(2-hydroxyethyl methacrylate) (PHEMA), polyvinyl alcohol, agarose, chitosan, polyethyleneglycol, albumin, and combinations thereof, the culture surface being a surface in contact with cells.

11. The method of claim 1, wherein the hepatic endoderm cell:the vascular cell:and the mesenchymal cell are co-cultured at a ratio of from 10:5:1 to 10:10:2, and the cells are seeded at a density of 20 to 2000 cells per microchamber.

12. The method of claim 1, wherein
the microchamber has a bottom portion and an opening,
the opening is defined by a wall that surrounds an area from a boundary between the opening and the bottom portion to an end of the opening, the wall having a taper angle in a range from 1 to 20 degrees, and
the bottom portion has a hemispherical shape or a truncated cone shape.

13. The method of claim 1, wherein the expression levels of the genes in the tissue structure, in the biological tissue sampled from the adult, and the biological tissue sampled from the fetus are analyzed by using a DNA chip on which segments of the genes are immobilized.

14. The method of claim 1, wherein the co-culturing comprises:
forming an aggregate of the hepatic endoderm cell, the vascular cell, and the mesenchymal cell;
forming an organ bud from the aggregate; and
further culturing the organ bud for maturation.

15. The method of claim 14, wherein the forming of an organ bud and further culturing are performed such that the cells in the organ bud remain aggregated.

16. The method of claim 14, wherein the forming of an aggregate is performed such that the aggregate forms a cluster having a spheroid shape, and the forming of an organ bud and the further culturing are performed such that the spheroid shape is maintained.

* * * * *

UNITED STATES PATENT AND TRADEMARK OFFICE
CERTIFICATE OF CORRECTION

| | | |
|---|---|---|
| PATENT NO. | : 11,060,065 B2 | Page 1 of 1 |
| APPLICATION NO. | : 14/897161 | |
| DATED | : July 13, 2021 | |
| INVENTOR(S) | : Yoko Ejiri et al. | |

It is certified that error appears in the above-identified patent and that said Letters Patent is hereby corrected as shown below:

In the Claims

In Column 23, Line 23, Claim 1, delete "Pearson-product moment" and insert -- Pearson product-moment --, therefor.

In Column 24, Line 26, Claim 11, delete "cell:the" and insert -- cell, the --, therefor.

In Column 24, Line 26, Claim 11, delete "cell:and" and insert -- cell, and --, therefor.

Signed and Sealed this
Fourteenth Day of January, 2025

Derrick Brent
*Acting Director of the United States Patent and Trademark Office*